(12) United States Patent
Bates

(10) Patent No.: US 8,702,744 B2
(45) Date of Patent: Apr. 22, 2014

(54) APPARATUS AND METHODS FOR RENAL STENTING

(75) Inventor: Mark C. Bates, Charleston, WV (US)

(73) Assignee: Nexeon MedSystems, Inc., Charleston, WV (US)

( * ) Notice: Subject to any disclaimer, the term of this patent is extended or adjusted under 35 U.S.C. 154(b) by 1023 days.

(21) Appl. No.: 11/125,448

(22) Filed: May 9, 2005

(65) Prior Publication Data

US 2006/0253186 A1    Nov. 9, 2006

(51) Int. Cl.
*A61M 29/00* (2006.01)

(52) U.S. Cl.
USPC .......... 606/192; 623/1.11; 604/96.1; 604/529

(58) Field of Classification Search
USPC .............. 604/101.01, 103.07, 509, 35, 96.01, 604/101.3, 101.05, 529, 103.1; 606/200, 606/191–198; 623/1.11, 1.12, 23.65, 23.7, 623/1.23; 600/424
See application file for complete search history.

(56) References Cited

U.S. PATENT DOCUMENTS

| | | | | |
|---|---|---|---|---|
| 3,885,561 | A * | 5/1975 | Cami | 604/247 |
| 4,580,568 | A | 4/1986 | Gianturco | |
| 4,655,771 | A | 4/1987 | Wallsten | |
| 4,723,549 | A | 2/1988 | Wholey et al. | |
| 4,733,665 | A | 3/1988 | Palmaz | |
| 4,838,879 | A * | 6/1989 | Tanabe et al. | 604/529 |
| 5,325,845 | A * | 7/1994 | Adair | 600/114 |
| 5,749,890 | A | 5/1998 | Shaknovich | |
| 5,776,141 | A * | 7/1998 | Klein et al. | 623/1.11 |
| 5,814,064 | A | 9/1998 | Daniel et al. | |
| 5,833,650 | A | 11/1998 | Imran | |
| 5,876,374 | A | 3/1999 | Alba et al. | |
| 6,036,682 | A * | 3/2000 | Lange et al. | 604/529 |
| 6,270,489 | B1 * | 8/2001 | Wise et al. | 604/508 |
| 6,295,989 | B1 | 10/2001 | Connors | |
| 6,364,900 | B1 * | 4/2002 | Heuser | 623/1.11 |
| 6,423,032 | B2 | 7/2002 | Parodi | |
| 6,443,926 | B1 * | 9/2002 | Kletschka | 604/96.01 |
| 6,485,500 | B1 * | 11/2002 | Kokish et al. | 606/194 |
| 6,488,702 | B1 | 12/2002 | Besselink | |

(Continued)

FOREIGN PATENT DOCUMENTS

| | | |
|---|---|---|
| EP | 0917886 A1 | 5/1999 |
| WO | WO 00/54829 A2 | 9/2000 |
| WO | WO 2004/107965 A2 | 12/2004 |

OTHER PUBLICATIONS

PCT International Search Report for PCT/US06/17986, 2 pages (mailed Jan. 31, 2008).

(Continued)

*Primary Examiner* — Darwin Erezo
*Assistant Examiner* — Katrina Stransky
(74) *Attorney, Agent, or Firm* — Foley & Lardner LLP; Nicola A. Pisano; Christopher C. Bolten

(57) ABSTRACT

The present invention provides and apparatus and methods for emboli removal and stenting within the renal arteries having a catheter system having a distal occlusion element, a stent deployment section, and an emboli removal lumen. The occlusion element is disposed at a predetermined distance from the stent deployment section specific for use in the renal artery, and is constructed to reduce the potential for perforation or jailing during stent deployment. The apparatus further includes an array of radio-opaque markers disposed on the stent delivery catheter to facilitate accurate stent deployment within a renal artery.

26 Claims, 4 Drawing Sheets

(56) References Cited

U.S. PATENT DOCUMENTS

| | | |
|---|---|---|
| 6,514,237 B1 | 2/2003 | Maseda |
| 6,540,712 B1 | 4/2003 | Parodi et al. |
| 6,579,311 B1 * | 6/2003 | Makower .................... 623/1.23 |
| 6,596,011 B2 * | 7/2003 | Johnson et al. .............. 606/200 |
| 6,641,573 B1 | 11/2003 | Parodi |
| 6,765,144 B1 | 7/2004 | Wang et al. |
| 6,852,116 B2 * | 2/2005 | Leonhardt et al. ............ 606/108 |
| 6,960,222 B2 * | 11/2005 | Vo et al. ........................ 606/200 |
| 6,972,030 B2 * | 12/2005 | Lee et al. ...................... 623/1.11 |
| 2002/0026145 A1 * | 2/2002 | Bagaoisan et al. ......... 604/96.01 |
| 2002/0065507 A1 * | 5/2002 | Zadno-Azizi ................ 604/509 |
| 2002/0169436 A1 * | 11/2002 | Gurm et al. ................... 604/509 |
| 2004/0049152 A1 * | 3/2004 | Nayak ....................... 604/96.01 |
| 2004/0060563 A1 * | 4/2004 | Rapacki et al. .......... 128/207.14 |
| 2004/0064042 A1 * | 4/2004 | Nutting et al. ................ 600/435 |
| 2004/0068285 A1 | 4/2004 | Burgmeier et al. |
| 2004/0093056 A1 * | 5/2004 | Johnson et al. .............. 623/1.11 |
| 2004/0267195 A1 * | 12/2004 | Currlin ....................... 604/103.1 |
| 2005/0027247 A1 * | 2/2005 | Carrison et al. ......... 604/101.01 |
| 2005/0186243 A1 | 8/2005 | Hunter et al. |
| 2006/0008606 A1 * | 1/2006 | Horn et al. ................... 428/36.1 |
| 2006/0032508 A1 * | 2/2006 | Simpson ....................... 128/898 |

OTHER PUBLICATIONS

PCT Written Opinion of the International Searching Authority for PCT/US06/17986, 6 pages (mailed Jan. 31, 2008).

* cited by examiner

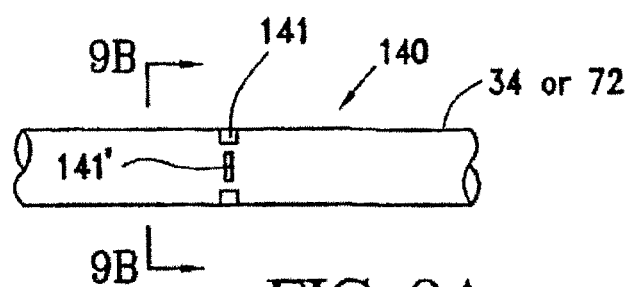 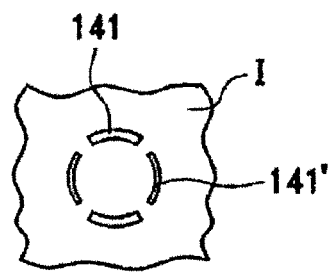
FIG. 9A  FIG. 9B
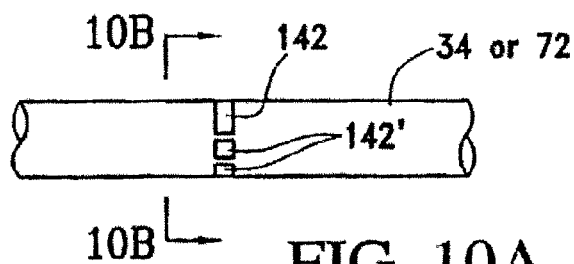 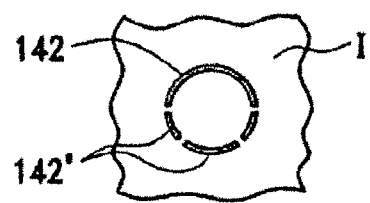
FIG. 10A  FIG. 10B
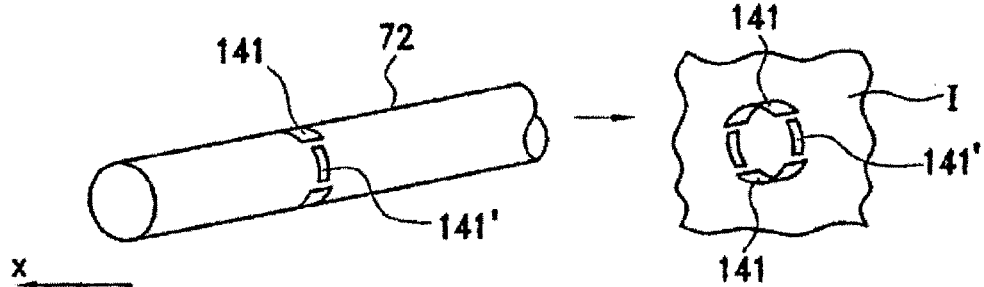
FIG. 11A
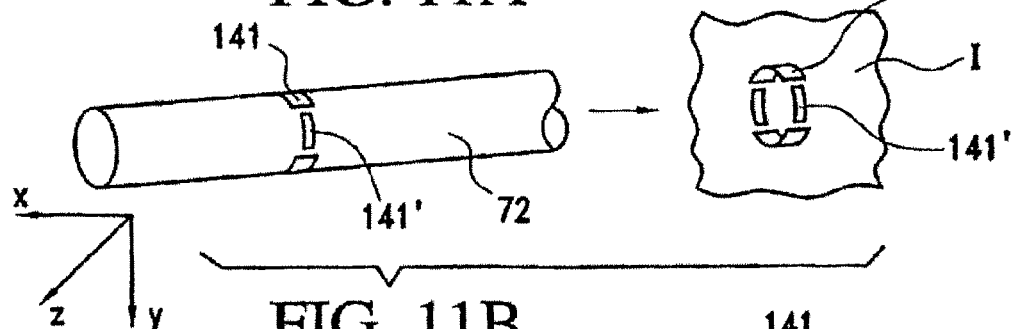
FIG. 11B
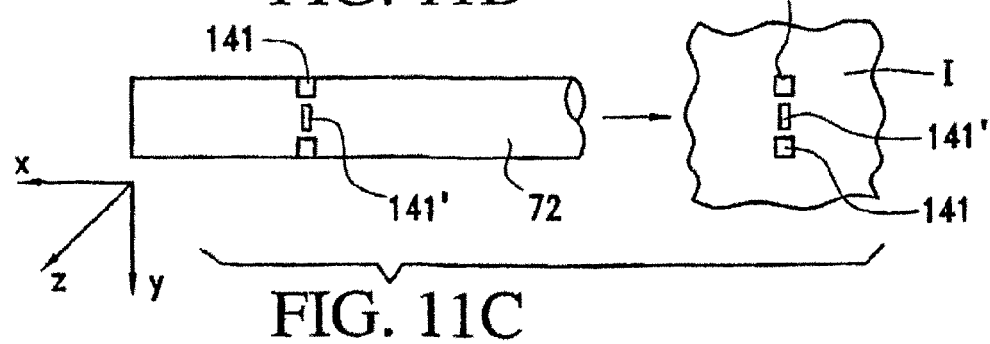
FIG. 11C

APPARATUS AND METHODS FOR RENAL STENTING

FIELD OF THE INVENTION

The present invention relates to apparatus and methods for delivering vascular prostheses, such as stents, within the renal arteries. More particularly, the present invention relates to a vascular prosthesis and delivery system for delivering the vascular prosthesis that reduce the risk of embolization arising from balloon dilatation and/or stenting of a renal artery stenosis.

BACKGROUND OF THE INVENTION

Stenting is now a commonly accepted procedure to maintain the patency of vessels following angioplasty, and has gained widespread acceptance for the treatment of blockages of the cardiac arteries. Numerous stent designs are known in the prior art, including balloon expandable slotted tube stents, such as described in U.S. Pat. No. 4,733,665 to Palmaz, radially self-expanding zig-zag structures, such as described in U.S. Pat. No. 4,580,568 to Gianturco, and self-expanding wire-mesh structures, such as described in U.S. Pat. No. 4,655,771 to Wallsten. Each of these previously-known stents provides a mix of ease-of-delivery and deployment, radial strength, crush resistance and other characteristics.

Despite the wide variety of stent structures available, there are certain vessels within the body that pose unique challenges for previously-known stent and stent delivery system designs. One such vessel is the renal artery. The relatively short length of the renal artery and the manner in which it branches from the abdominal aorta, often make access and deployment of previously-known stents difficult. Because renal artery lesions often occur at the renal ostium, the treatment of such lesions pose unique problems relating to embolization of plaque liberated during angioplasty. In addition, deployment of a stent across an ostial lesion can result in a portion of the stent extending into the abdominal aorta that may serve as a site of thrombus formation and also make re-access to the vessel virtually impossible.

A number of catheter-based systems are known that attempt to address the problem of embolization resulting from the disruption of plaque during balloon dilatation. Such systems may be independent of the stent delivery system or form a part thereof, and generally may be classified as either "proximal" or "distal" emboli protection systems. Proximal emboli protection systems, such as described in U.S. Pat. No. 5,833,650 to Imran et al. and U.S. Pat. No. 6,295,989 to Connors, generally place an occlusion element upstream of a lesion to prevent antegrade blood flow through the vessel during angioplasty; suction is applied to aspirate emboli-laden blood proximally through the catheter prior to restoring antegrade flow. Distal emboli protection systems, such as described in U.S. Pat. No. 4,723,549 to Wholey and U.S. Pat. No. 5,814,064 to Daniel et al. employ a blood permeable filter element that is placed downstream of the stenosis to filter emboli released during angioplasty.

Currently, none of the foregoing previously-known emboli protection systems perform reliably when used in renal artery angioplasty or stenting. For example, due to the relatively short length of the renal artery, there may be insufficient distance to deploy the filter element of a distal emboli protection system. In such cases, the perimeter of the filter element may not positively seal against the vessel wall, thereby permitting emboli to bypass the filter element and travel downstream to lodge in, and occlude, smaller vessels.

In addition, the relatively short length of the renal artery makes it difficult to place a filter in the renal artery. The filter frame and/or filter material typically make the filter axially stiff and impede tracking of the filter around the steep angulation at the renal ostium. The renal artery often has an inferior angle of origin from the aorta and then immediately projects posteriorly, thereby further amplifying difficulty in accessing the renal artery from a femoral artery approach.

Further, most filter designs employ a retrieval catheter that is advanced over the filter to contract the filter prior to removal. Such retrieval catheters may not conform to the wire and may get caught on the filter, thereby rendering retrieval impossible. In such cases the filter must be forcibly removed, with the attendant risk that the filter may become entangled in the stent and/or traumatize the artery requiring emergent surgical repair.

A wire having a distal occlusion balloon, such as described in the above patent to Connors, presents similar drawbacks in renal artery applications. For example, the presence of the balloon changes the axial stiffness of the wire and enhances the difficulty in tracking across severe angle encountered at the renal ostium. In addition, inflation of the distal balloon applies tension to the wire that may inflict trauma on the renal artery when a stent delivery catheter is then advanced around the abrupt angle bend at the renal artery ostium. A further drawback common to both the distal occlusion balloon and filter systems is the presence of the balloon or filter wire, which may limit the clinician's options when accessing and treating complex lesions.

Still other problems may arise in attempting to use a distal balloon emboli protection system in a renal artery. Again, because of the relatively short length of the renal artery, it is possible to dislodge the distal occlusion element during manipulation of the angioplasty balloon catheter and/or stent delivery system, thus permitting emboli to bypass the occlusion element. While the potential for dislodging the occlusion element, e.g., balloon, may be reduced by use of a compliant balloon, such use raises other potential problems. Specifically, use of a compliant balloon enhances the risk of perforating or "jailing" the balloon during stent deployment. In the former case the balloon may inadvertently deflate, enabling the emboli to bypass the balloon and flow downstream. In the latter situation, the stent traps a portion of the balloon against the vessel wall, making it difficult or impossible to retrieve the occlusion element and necessitating surgical intervention.

Eighty percent of renal artery lesions are ostial and thus proximal balloon protection systems will not work in the majority of cases. The majority of the remaining "non-ostial" renal artery lesions occur within the first centimeter of the renal origin. In such cases, proximal balloon occlusion may be employed in only a very small number of patients. Accordingly, the use of previously-known proximal protection systems during renal stenting is not viable solution.

As noted above, still other problems have limited the acceptance of stenting in the treatment of renal artery disease. These problems arise both from the anatomy of the vessel and the types of lesions that are observed. Not only is the renal artery relatively short, but it also is difficult to access from percutaneous access sites in the groin region, because the arteries tend to branch in a descending manner from the abdominal aorta. As a result, it is often difficult to visualize the arteries under fluoroscopic guidance, and even more difficult to determine accurate placement of a stent delivery system in such vessels.

Because many renal artery lesions occur at the ostia of the vessels as noted above, inaccurate stent placement may result in either incomplete coverage of the lesion (with attendant restenosis) or the stent may project excessively into the abdominal aorta and serve as a site of thrombus formation. In addition, in the latter case the projecting portion of the stent may make further access to that renal artery impossible. Although some attempts for addressing these issues have been made, such as disclosed in U.S. Pat. No. 5,749,890 to Shaknovich, such systems do not permit the clinician to precisely determine the location and orientation of the stent delivery system relative to the ostium prior to stent deployment.

To date, the successful use of stents to treat renal artery obstructions has been limited to a relatively few clinicians with extraordinary skill gained from extensive experience in this area. It therefore would be desirable to provide apparatus and methods that enable a broader cross-section of interventional clinicians to effectively treat renal artery disease.

Accordingly, it would be desirable to provide apparatus and methods that enable removal of emboli liberated during balloon dilatation or other treatment of the renal artery, and that account for the peculiar anatomy of that vessel.

It further would be desirable to provide apparatus and methods that permit an emboli protection system to be used in conjunction with angioplasty and stenting of the renal arteries with reduced risk of complications.

It further would be desirable to provide apparatus and methods that facilitate accurate determination of stent placement within a renal artery prior to deployment of a stent.

SUMMARY OF THE INVENTION

In view of the foregoing, it is an object of the present invention to provide apparatus and methods that enable removal of emboli liberated during balloon dilatation or other treatment of the renal artery, and that account for the peculiar anatomy of that vessel.

It is a further object of this invention to provide apparatus and methods that permit an emboli protection system to be used in conjunction with angioplasty and stenting of the renal arteries with reduced risk of complications.

It is another object of the present invention to provide apparatus and methods that facilitate accurate determination of stent placement within a renal artery prior to deployment of a stent.

These and other objects of the present invention are accomplished by providing apparatus and methods for emboli removal and stent delivery that are specifically designed to address the challenges presented by the treatment of renal artery disease. The apparatus of the present invention preferably comprises a catheter system having a distal occlusion element, stent deployment section, and an emboli removal lumen.

In accordance with the principles of the present invention, the occlusion element is disposed at a distance from the stent deployment section selected for use in the renal artery, and is constructed to reduce the potential for perforation or jailing during stent deployment. The occlusion element is employed in conjunction with the emboli removal lumen to aspirate emboli collected proximally of the occlusion element during angioplasty and/or stenting. The catheter further comprises an array of radio-opaque markers that are disposed on the catheter so as to provide accurate information regarding the location and orientation of the stent under fluoroscopic visualization.

In accordance with a first aspect of the present invention, the occlusion element comprises a balloon of heterogenous compliancy, so that a proximal portion of the balloon is stiffer, when deployed, than a distal portion of the balloon. This asymmetry in the compliance of the balloon reduces the risk of balloon perforation or jailing during stent deployment. Further, the occlusion element may have a shape configured to reduce dislodgement during manipulation of the apparatus. Alternatively, or in addition, the occlusion element also may include structural features, such as a plurality of longitudinally-extending struts, that further protect the proximal portion of the occlusion element.

As a further alternative, the occlusion element may include an interior portion that extends within the guide wire lumen of the catheter and an aperture in the lateral wall of the catheter between the occlusion element and the stent delivery portion of the catheter. This provides an alternative path for particle retrieval. Specifically, the guide wire can be temporally removed after positioning the catheter in the target area. In this manner, when the occlusion element is deployed, the interior portion occludes the guide wire lumen distal to the aperture, permitting blood and emboli to be preferentially aspirated via the aperture through the proximal portion of the guide wire lumen. Stagnant flow in the stented area and debris thus may be cleared without advancing the guide catheter or sheath over the stent delivery balloon.

In accordance with another aspect of the present invention, the catheter includes a plurality of radio-opaque markings disposed on the circumference of the catheter that permit the spatial orientation of the catheter to be reliably determined under fluoroscopic visualization. The markings may consist of a single feature or multiple features that may be used to align the apparatus within the renal artery, and thus reduce the likelihood of inaccurate stent placement.

Methods of using the apparatus of the present invention to reduce embolization in connection with stenting of the renal arteries, and improving the accuracy of stent placement, also are provided.

BRIEF DESCRIPTION OF THE DRAWINGS

The above and other objects and advantages of the present invention will be apparent upon consideration of the following detailed description, taken in conjunction with the accompanying drawings, in which like reference numerals refer to like parts throughout, and in which:

FIGS. 9A-9B are side and cross-sectional views, respectively, of a pattern of radio-opaque markers for use in positioning the apparatus of the present invention;

FIGS. 10A-10B are side and cross-sectional views, respectively, of an alternative pattern of radio-opaque markers in accordance with the present invention; and FIGS. 11A-11C are views depicting a method of positioning the apparatus using the radio-opaque marking pattern on FIG. 9.

DETAILED DESCRIPTION OF THE INVENTION

The present invention is directed to apparatus and methods for treating renal artery disease, and in particular, for removing obstructions of the renal arteries with reduced risk of embolization. Due to the relatively short length of the renal arteries, renal stenting to address obstruction is performed by only a relatively few interventional clinicians, each of whom has acquired extraordinary skill gained from extensive experience in this area. The numerous technical challenges posed by such stenting in view of previously-known apparatus and methods has limited widespread adoption of this treatment. The present invention addresses these issues by providing specialized apparatus for use in renal artery stenting.

Figure 1:
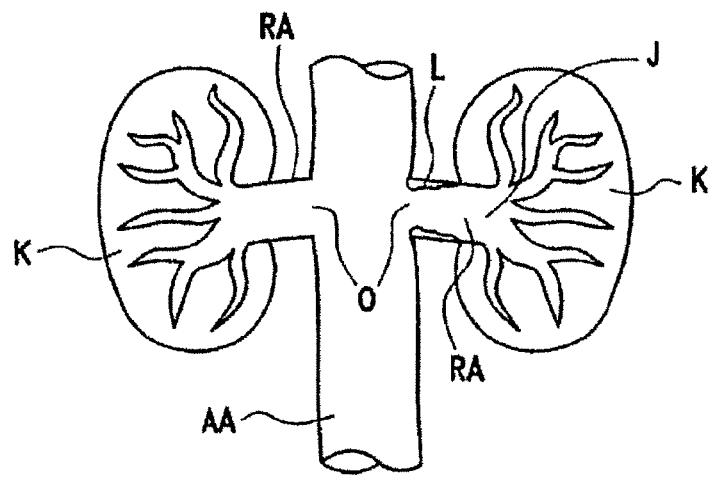
FIG. 1 is a schematic view of a renal artery and portion of the abdominal aorta depicting a lesion at the renal artery ostium.

Referring to FIG. 1, the anatomy of the human renal artery RA is depicted. The artery generally branches at a descending angle from the abdominal aorta AA, thus making access to the vessel difficult from below via the femoral arteries. The length of the artery from ostium O to junction J that branches into the lesser arteries of the kidney K is relatively short, and varies from about 0.5 to 2.5 cm in human adults. Ostial lesion L is shown disposed at the entrance to the renal artery and extending slightly into abdominal aorta AA. Lesion L is typical of the obstructions encountered in renal artery disease, and can exacerbate the difficulty in guiding a catheter into the renal artery.

As noted in the preceding sections of this specification, a common hazard attendant upon angioplasty or stenting is the liberation of emboli that can travel downstream and occlude smaller vessels. A number of devices are known in the prior art that attempt to address this problem. Generally the previously-known devices may be categorized as either "distal protection systems" or "proximal protection systems." FIGS. 2 and 3 illustrate the problems encountered using such systems in the context of renal artery stenting.

Figure 2A:
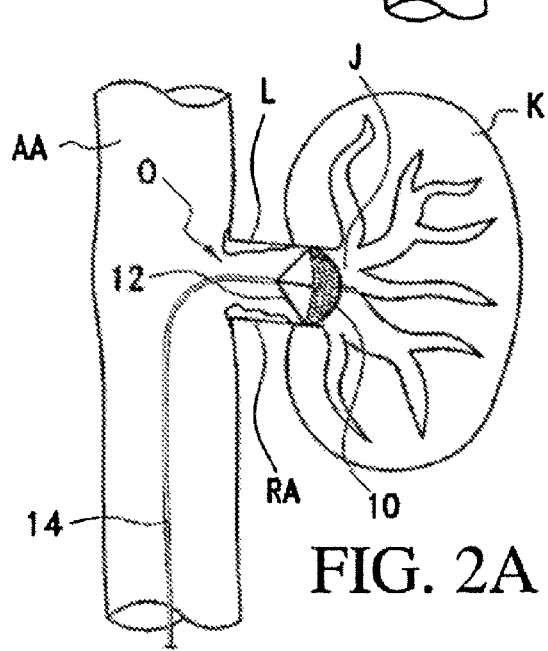
FIGS. 2A-2B are schematic views depicting the disadvantages of attempting to use a previously-known distal emboli protection system during interventional treatment of the lesion of FIG. 1.
Figure 2B:
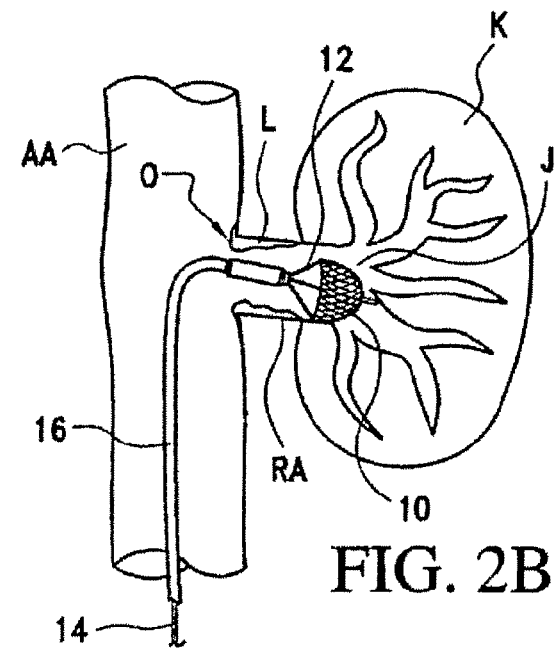

Referring to FIGS. 2A and 2B, a guide-wire based filter, such as described in U.S. Pat. No. 5,814,064 to Daniel et al. is depicted. In the device disclosed in that patent, filter element 10 is disposed from a plurality of radially-expanding struts or coil 12 coupled to guide wire 14. In FIG. 2A, filter element 10 is shown deployed in renal artery RA just proximal to junction J. Due to the relatively short length of the artery, however, insertion of angioplasty catheter or stent delivery system 16 over guide wire 14 interferes with deployment of filter element 10. Specifically, advancement of catheter 16 may either partially collapse struts 12 or cause the filter element to become tilted relative to the longitudinal axis of the artery. In either case, emboli created during use of catheter 16 will bypass filter element 10 and present a risk of obstruction of smaller renal vessels or worse injure the distal vessel.

Figure 3A:
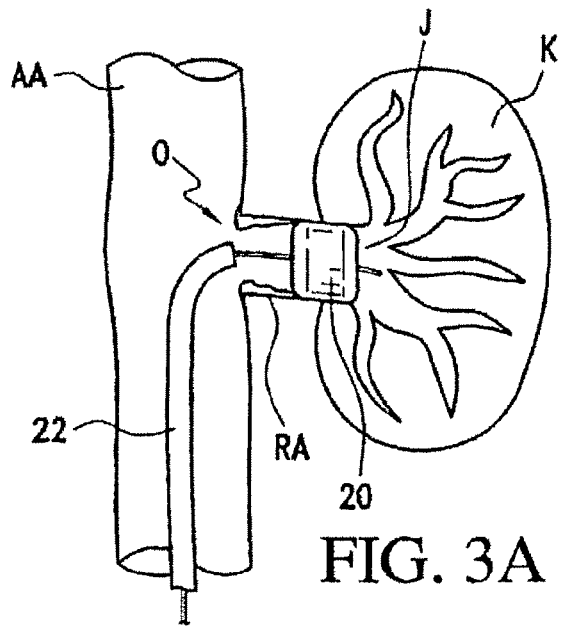
FIGS. 3A-3B are schematic views depicting jailing of the balloon of a distal balloon emboli protection system during stenting.
Figure 3B:
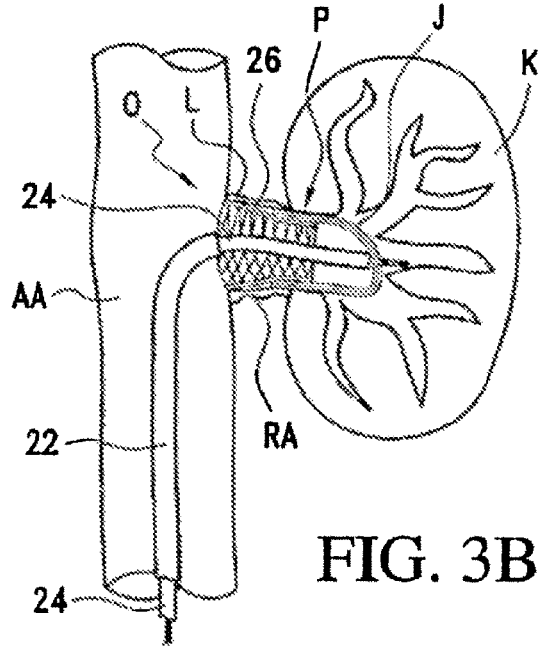

FIGS. 3A and 3B illustrate problems that have arisen during use of distal balloon occlusion protection systems in conjunction with angioplasty or stenting of renal artery RA. FIG. 3A depicts guide-wire based occlusion element 20, illustratively a compliant balloon, deployed in the artery at a location distal to lesion L and proximal of junction J. Occlusion balloon 20 is deployed to arrest antegrade flow through the artery during angioplasty or stenting, and is used in conjunction with a proximal catheter 22, such as described in U.S. Pat. No. 6,295,989 to Connors. Catheter 22 includes a lumen through which emboli may be aspirated during and after the angioplasty or stenting procedure, and before the occlusion element is deflated to re-establish antegrade flow through the artery.

As a result of the short distance available within which to deploy occlusion element 20, incidents have been encountered wherein the distal end of angioplasty or stenting catheter 24 interferes with proper functioning of the occlusion element and causes the proximal portion of the occlusion element to become everted, that is, concave in the proximal direction. Such interference may arise either from having the distal end of catheter 24 physically dislodging or perforating occlusion element 20, or from transfer of motion from catheter 24 to occlusion element 20 during manipulation of the catheter. Any of these situations can vitiate the usefulness of the occlusion element by permitting emboli to bypass the occlusion element.

In addition, as specifically illustrated in FIG. 3B, deployment of the stent may result in an everted proximal portion P of occlusion element 20 becoming trapped against the wall of the vessel by the stent 26 (so called "jailing" of the occlusion element). Subsequently, it may not be possible to remove occlusion element 20 without tearing the occlusion element or potentially damaging the vessel. The apparatus and methods of the present invention are designed to overcome the foregoing disadvantages of previously-known systems.

Figure 4A:
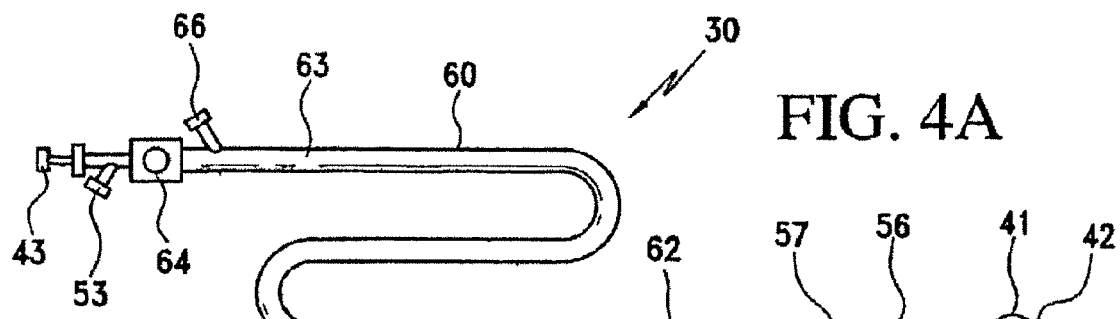
FIGS. 4A-4B are side views of the apparatus constructed in accordance with the principles of the present invention for use in stenting renal arteries.
Figure 4B:
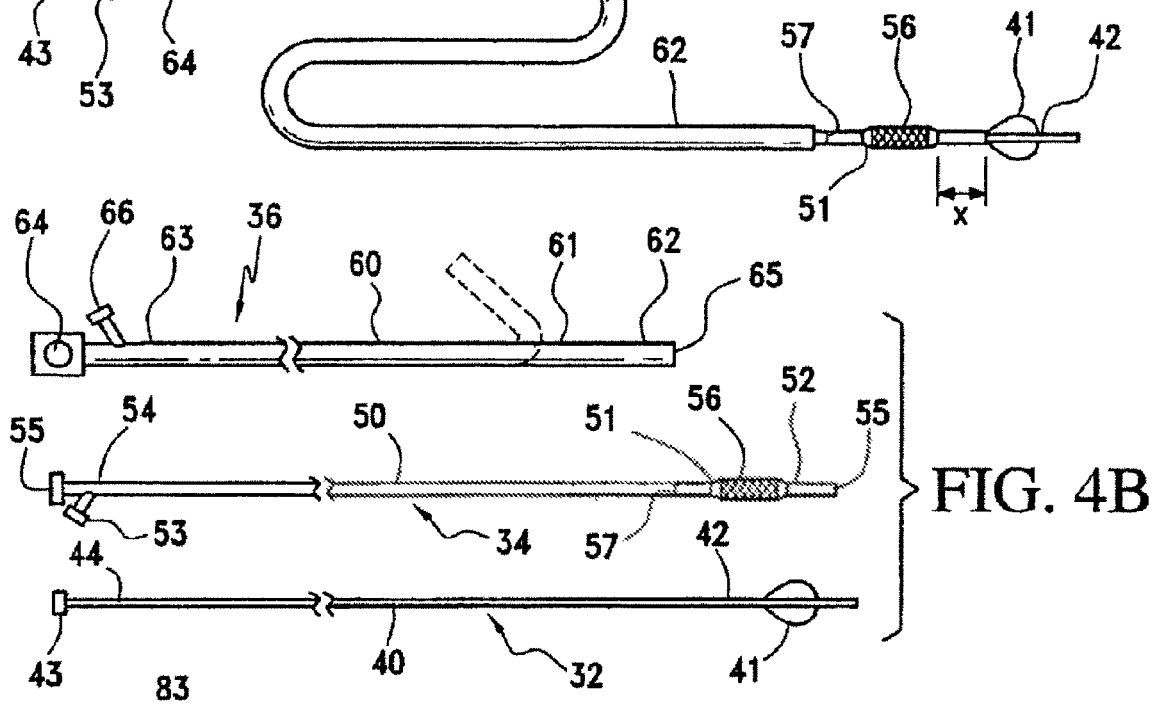

Referring now to FIG. 4, a first embodiment of apparatus 30 for renal artery stenting and emboli protection system is described. Apparatus 30 comprises occlusion device 32, angioplasty or stent delivery catheter 34 and guide catheter 36, each specifically proportioned for use in the renal arteries.

Occlusion device 32 preferably comprises flexible polymer or metal tube 40 having inflatable occlusion element 41 disposed adjacent to distal end 42 and inflation port 43 at proximal end 44. Tube 40 includes an inflation lumen that extends along the length of device 32 to provide fluid communication from proximal end 44 to the interior of occlusion element 41. Occlusion device may be constructed as described, for example, in U.S. Pat. No. 6,641,573 to Parodi or U.S. Pat. No. 6,423,032 to Parodi et al. In accordance with the principles of the present invention, occlusion element 41 is configured to reduce the risk of dislodgement, perforation or jailing, as described in greater detail below.

Angioplasty or stent delivery catheter 34 may be of any type appropriate to perform angioplasty of a renal artery lesion and/or to deliver a suitable stent of the types described hereinabove. Use of a bistable cell-structure, of the type described in U.S. Pat. No. 6,488,702 to Besselink, may be especially advantageous due to the high structural rigidity such stents provide. Catheter 34 illustratively includes catheter shaft 50 having balloon 51 disposed near distal end 52 and balloon inflation port 53 disposed on proximal end 54. Inflation port 53 is coupled in fluid communication to the interior of balloon 51 via an inflation lumen. Catheter shaft 50 further includes interior lumen 55 that permits catheter 34 to be advanced over the exterior of occlusion device 32. Stent 56 may be disposed on balloon 51 for deployment in the renal artery to maintain the patency of the vessel. In accordance with one aspect of the present invention, catheter 50 includes pattern 57 of radio-opaque markers that facilitate proper positioning of the catheter (and stent, if present) within the renal artery, as described in greater detail below.

Further in accordance with the principles of the present invention, occlusion device 32 and catheter 34 are configured so that when catheter 34 is fully advanced over tube 40 of occlusion device 32 in the distal direction, the distal shoulder of balloon 51 is disposed at a predetermined minimum distance x from the proximal shoulder of occlusion element 41. Distance x is selected during manufacture to correspond to the minimum distance required for the assembled device to be positioned within a human renal artery without having balloons 51 and 81 interfere with one another, e.g., 0.5 cm. Preferably, occlusion devices 32 and catheters 34 may be manufactured in matched sets so that distance x falls within a specified range, such as 0.5 to 2.5 cm, so that apparatus 30 may be selected appropriate for the anatomy of a given patient.

Guide catheter 36 comprises a flexible and preferably steerable catheter 60 that is configured to be inserted percutaneously and transluminally in a retrograde manner through the abdominal aorta via a femoral access site. Catheter 60 preferably comprises an articulable distal region 61 that may be bent in-situ within the abdominal aorta to dispose distal end 62 to provide access to a renal artery. For example, catheter 60 may include a pull-wire coupled to a point on the circumference of distal end 62, so that retraction of the pull wire causes the distal end of the catheter to deflect (as shown in dotted lines in FIG. 4B), as is known in the art. Proximal end 63 of catheter 60 further comprises control knob 64 coupled to the pull wire to selectively cause distal region 61 to deflect.

Guide catheter 60 includes central lumen 65 that permits angioplasty or stent delivery catheter 34 to be advanced therethrough, and suction port 66. When catheter 34 is disposed within the central lumen of the guide catheter, lumen 65 forms an annulus through which suction may be drawn to aspirate emboli-laden blood through distal end 62 via suction port 66. In addition, in lieu of a pull-wire arrangement, guide catheter alternatively may include one of more interchangeable stylets configured to orient and properly position the distal end relative to the renal artery ostium. As a further alternative, guide catheter 60 may comprise electrically controllable materials such as electroactive polymers, such as described in U.S. Pat. No. 6,514,237 to Maseda. Lastly, any available renal guide catheters could be used with standard proximal connectors that will allow injection of contrast and flush or aspiration of debris.

Figure 5A:
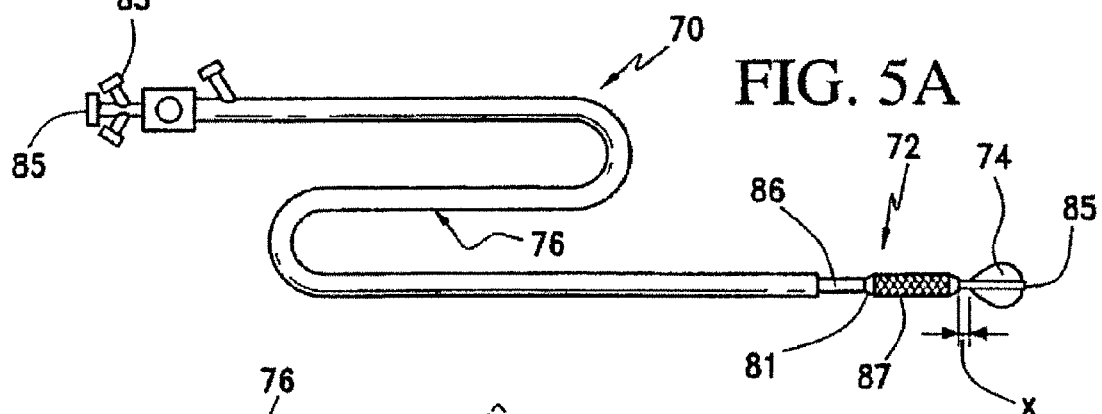
FIGS. 5A-5B are side views of alternative apparatus of the present invention for use in stenting renal arteries.
Figure 5B:
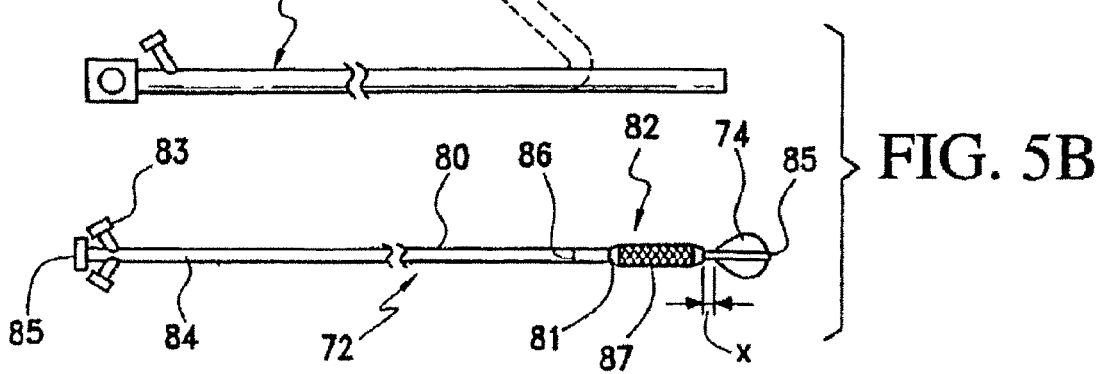

Referring now to FIG. 5, an alternative embodiment of apparatus 70 of the present invention is described. Apparatus 70 includes angioplasty or stent delivery catheter 72 having occlusion element 74 disposed on its distal end, and guide catheter 76. Catheter 72 combines the functions of occlusion device 32 and angioplasty or stent delivery catheter 34 of the embodiment of FIG. 5. Guide catheter 76 may be as described for the embodiment of FIG. 4 above, and includes an articulable distal region actuated by a control knob and a suction port.

Construction of catheter 72 may be similar to that described above for catheter 34 of the embodiment of FIG. 4, and includes catheter shaft 80 having balloon 81 disposed in distal region 82. Inflation port 83 is disposed on proximal end 84, and is coupled in fluid communication to the interior of balloon 81 via an inflation lumen. Guide wire lumen 85 extends from the proximal to the distal ends of catheter 80 to permit the catheter to be advanced over a conventional guide wire. Stent 87 may be disposed on balloon 81 for deployment in the renal artery to maintain the patency of the vessel.

In accordance with the present invention, catheter 80 in addition carries occlusion element 74, and pattern 86 of radio-opaque markers that facilitate proper positioning of the catheter (and stent, if present) within the renal artery. Occlusion element 74 may be constructed as described in greater detail below, and is disposed in distal region at a predetermined distance x from the distal shoulder of the angioplasty or stent delivery balloon 81. Specifically, distance x is selected so that deployment of balloon 81 will not interfere with proper functioning of occlusion element 74. Individual catheters 80 may be manufactured with a distance x selected from within a specified range, such as 0.2 to 2.5 cm, so that catheter may be selected appropriate for the anatomy of a given patient.

Referring now to FIGS. 6 and 7, various embodiments of occlusion elements suitable for use in the apparatus of FIGS. 4 and 5 are described. In a first family of embodiments, illustrated in FIG. 6, the occlusion element comprises a balloon having an asymmetric shape or thickness. In the embodiments of FIG. 7 the occlusion element further comprises an additional protective feature external of the balloon. As will be understood by one of skill in the art of catheter design, occlusion elements depicted in FIGS. 6 and 7 correspond to occlusion element 41 of the apparatus of FIG. 4 or occlusion element 74 of the apparatus of FIG. 5.

Figure 6A:
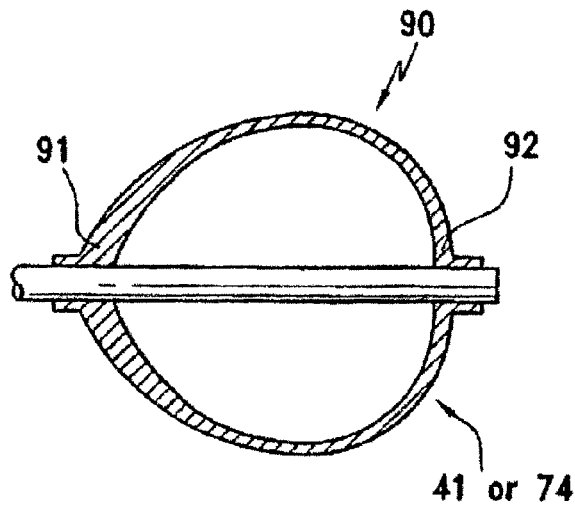
FIGS. 6A-6B are side views, partly in section, of alternative embodiments of occlusion elements constructed in accordance with the principles of the present invention.

More particularly, in the embodiment of FIG. 6A, balloon 90 comprises a compliant or semi-compliant material, such as nylon. Balloon 90 has an asymmetric shape resulting from longitudinal variation in the thickness of the balloon from proximal shoulder 91 to distal shoulder 92. Alternatively, the balloon may be molded to include ribs or other features that enhance the rigidity of the proximal portion of the balloon.

As depicted in FIG. 6A, the variation in thickness causes the balloon to expand preferentially in the distal direction when inflated. In accordance with the principles of the present invention, the relatively thicker proximal portion of the balloon will prevent the balloon from becoming everted if contacted by the balloon of the angioplasty or stent delivery system, thereby avoiding the "jailing" problem described above with respect to FIG. 3. Balloon 90 illustratively deploys to a bell shape, although other shapes may be employed, including spherical, pear-shaped and elliptical.

Figure 6B:
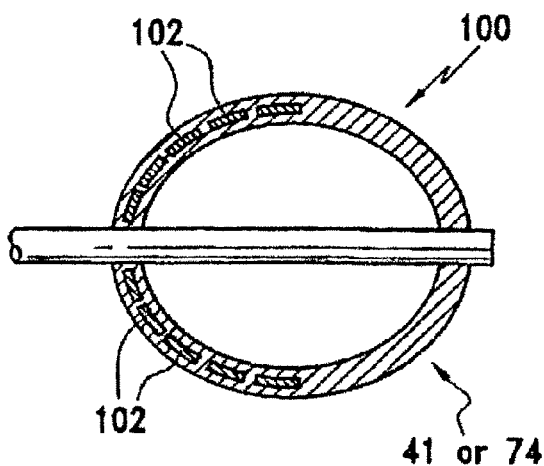

With respect to FIG. 6B, an alternative embodiment of a balloon suitable for use as the occlusion element of the apparatus of the present invention is described. Balloon 100 may be of uniform thickness or non-uniform thickness, and includes reinforcing matrix 102 embedded within the proximal portion of the balloon. For example, reinforcing matrix 102 may comprise a plurality of longitudinally-directed fiber strands or an open weave metal or polymer mesh. When balloon 100 is deployed, reinforcing matrix adds rigidity to the proximal portion of balloon 100, thereby reducing the risk that the balloon could become everted and jailed during stent deployment.

Figure 7A:
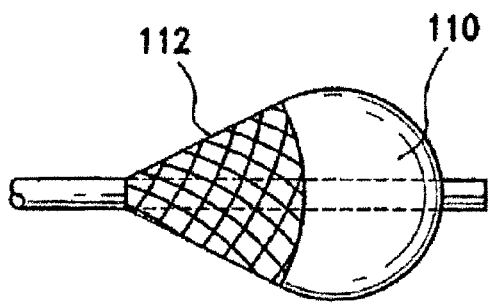
FIGS. 7A-7B are side views, partly in section, of further alternative embodiments of occlusion elements of the present invention that include external protective structures.

In FIG. 7, a second family of embodiments is described in which the occlusion element includes a separate protective structure disposed external to the balloon. In FIG. 7A, the external structure comprises expandable metal or polymer mesh 112 that covers the proximal portion of balloon 110 to prevent the balloon from everting.

Figure 7B:
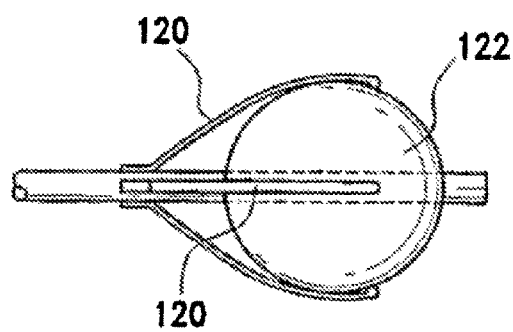

In FIG. 7B, the external structure comprises a plurality of flexible metal or polymer struts 120 that overlay the proximal portion of balloon 122 when deployed, and likewise prevent the angioplasty or stent delivery balloon from interfering with proper functioning of balloon 122. Illustratively, four struts 120 are disposed around the circumference of the catheter, although a greater or less number of such struts may be employed, depending upon size of circumference of the catheter and the size of the renal artery to be treated.

Figure 8A:
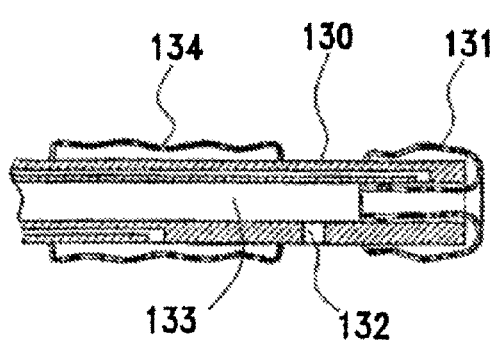
FIGS. 8A-8B are side sectional views of an embodiment of the catheter of the present invention wherein the guide wire lumen also may be used to aspirate blood and emboli from the renal artery.

With respect to FIG. 8A, a further optional feature of the catheter of the present invention is described. In lieu of, or in addition to, aspirating emboli-laden blood through the annulus between the guide catheter 76 and catheter 72, it may be desirable to aspirate blood from the space between occlusion element 74 and stent delivery balloon 81. This may be accomplished, for example, by occluding the distal opening of guide wire lumen 85 of catheter 72 and then drawing blood through an aperture that extends from the guide wire lumen through a lateral wall of catheter shaft 80.

Figure 8B:
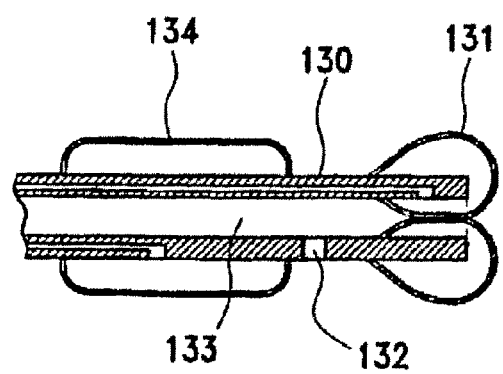

In FIG. 8A, a portion of the distal end of catheter shaft 130 is depicted which is suitable for implementing the foregoing feature. Compliant occlusion element 131 is affixed at one end to the exterior of the catheter shaft 130 and at the other end to the interior surface of catheter shaft 130. Aperture 132 extends through the lateral wall of catheter shaft 130 to provide communication between the exterior of the catheter shaft and guide wire lumen 133, and is disposed at a location distal of stent delivery balloon 134 and proximal of occlusion element 131. In FIG. 8B, when occlusion element 131 is deployed, the portion of the occlusion element that extends into guide wire lumen 133 inflates, thereby partially or fully occluding the guide wire lumen.

In operation, the clinician would first place a guide wire so that its distal end is disposed in a patient's renal artery. Catheter shaft 130 (corresponding, for example to catheter 72 of FIG. 5) may then be advanced along the guide wire so that the occlusion element and stent delivery system are disposed within the renal artery, as may be confirmed by fluoroscopic imaging. The guide wire may then be withdrawn and occlusion element 131 deployed.

Deployment of occlusion element 131 not only occludes antegrade flow through the artery, but also serves to occlude the distal opening of guide wire lumen 133. Once the stent has been delivered using balloon 134, Suction may be applied to the proximal end of catheter 76 to aspirate emboli-laden blood through aperture 132 and guide wire lumen 133. Alternatively, the guide wire may be left in position, so that the interior portions of occlusion element 131 seal against the guide wire when deployed.

In accordance with the above feature, emboli may be removed from the renal artery proximal of the occlusion element 131, but without aspirating blood in a retrograde manner through the distal opening of the guide wire lumen. Accordingly, construction of the catheter is simplified and ease of use enhanced. As will of course be understood, other arrangements may be employed to occlude guide wire lumen 133, and any number of apertures 132 may be provided through the lateral wall of catheter shaft 130.

Referring now to FIG. 9, another aspect of the apparatus of the present invention is described. As noted hereinabove, one of the difficulties of placing a stent in the renal artery is that if the stent is placed too far into the artery, it may provide incomplete coverage of the lesion. Alternatively, if the stent is placed with too large a portion projecting into the abdominal aorta, the proximal end of the stent may serve as a site of thrombus formation. In addition, the proximal portion of the stent may make subsequent re-entry of the renal artery very difficult.

The apparatus of the present invention overcomes these issues by providing a pattern of radio-opaque markers disposed in the distal region of the stent delivery catheter that are visible using well-known fluoroscopic systems and methods. Referring to FIGS. 8 and 9, exemplary embodiments of such patterns are described.

In FIGS. 9A and 9B, a first embodiment of radio-opague markers is described. Pattern 140 includes two long markers 141 and two short markers 141', made for example from gold or tantalum, disposed in alternating fashion around the circumference of catheter 34 or 72. Markers 141 and 141' permit the clinician to verify the longitudinal placement of the distal region of the catheter (and correspondingly, the stent) by examining the fluoroscopic image I (see FIG. 8B). In addition, variation in the length of the markers around the circumference of the catheter permits the clinician to verify the rotational movements of the catheter.

FIGS. 10A and 10B depict an alternative arrangement of markers including a single long marker 142 that spans half of the circumference of the catheter and three shorter markers 142' disposed on the remainder of the catheter circumference. These markings appear in the corresponding fluoroscopic image I as schematically indicated in FIG. 10B.

Operation of the apparatus of present invention is now described, illustratively with respect to apparatus 70 of FIG. 4. To treat a patient suffering from renal artery obstruction, the clinician would first create a percutaneous access site, e.g., by inserting a standard introducing catheter into the patient's femoral artery. Guide catheter 76 then is inserted through the introducing catheter and advanced into the patient's abdominal aorta. Using fluoroscopic guidance and a radio-opaque feature in the distal region of the guide catheter, the control knob on guide catheter is actuated to approximately align the distal end of the guide catheter with the ostium of the obstructed renal artery. Alternatively a standard guide catheter may be used to match the patient's anatomy. A conventional guide wire may then be advanced through the lumen of the guide catheter so that its distal end enters the renal artery.

Once the guide wire is placed in the renal artery, catheter 72 is advanced along the guide wire until stent 86 is disposed within the renal artery in apposition to the lesion. In particular, catheter 72 may be adjusted longitudinally or by rotating the catheter to bring the pattern of radio-opaque markers into alignment with the renal ostium. Occlusion element 74 is inflated to arrest antegrade flow through the artery.

Balloon 81 is inflated to deploy stent 87 against the wall of the renal artery and restore patency to the artery. Because balloons 81 and 74 are located at a predetermined distance x apart, both may be disposed within the short length of the renal artery without interfering with each other. During stent deployment, emboli released from the lesion are trapped by occlusion element 74. The stent deployment balloon then is deflated and the guide catheter is advanced over the proximal balloon through the stent while the distal balloon remains inflated. Suction then is applied to the suction port of guide catheter 76 to aspirate blood disposed within the renal artery. After the debris is cleared the distal, occlusion element 74 is deflated and flow is restored. Apparatus 70 and the guide wire then are withdrawn from the renal artery, permitting antegrade flow to become re-established through the unobstructed artery.

During placement of catheter in the renal artery as described above, the pattern of radio-opaque markings may be employed to confirm accurate positioning of the catheter within the artery and relative to the renal ostium. FIGS. 11A-11C provide schematic views that illustrate the relative orientation of the distal region of catheter 72 and the corresponding image created by the pattern of markers in fluoroscopic image I.

Assume, for example, that the clinician desires to align the longitudinal axis of the catheter parallel to the x-axis. The clinician may manipulate the longitudinal placement of catheter 72 and the angulation of guide catheter 76, to adjust the orientation of the distal end of catheter 72. In so doing, the clinician uses the degrees of alignment of the markers shown in the fluoroscopic image. In FIG. 11A, markings 141 and 141' create an elliptical pattern, indicating that the catheter is not aligned with the x-axis. In FIG. 11B, the catheter is more nearly in alignment with the x-axis, but still extends slightly in the z direction, producing a narrower ellipse in the fluoroscopic image. Finally, as depicted in FIG. 1C, as the catheter is brought completely into alignment with the x-axis, markers 141 and 141' form a line in the fluoroscopic image. The foregoing feature of the invention thus enables the clinician to more easily position the stent within the renal artery, thereby facilitating proper placement of the stent within the artery.

While preferred embodiments of the invention are described above, it will be apparent to one skilled in the art that various changes and modifications may be made. For example, it should be understood by those of skill in the art of interventional clinical practice that the emboli protection system may be employed in other applications, such as treatment of coronary, carotid saphenous femoral arteries and other vessels where the configuration of the vessel would limit the utility of previously known stent delivery and embolic protection systems. The appended claims are intended to cover all such changes and modifications that fall within the true spirit and scope of the invention.

What is claimed is:

1. A balloon catheter comprising:
   a catheter having proximal and distal ends, including a dilatation balloon disposed on the distal end and coupled to an inflation port at the proximal end by an inflation lumen,
   the catheter comprising an array of discrete dissimilarly shaped radio-opaque markers permanently affixed at the distal end, each of the markers in the array disposed equidistant from the distal end and aligned about a predetermined circumference of the catheter to facilitate determination of placement and angularity of the catheter relative to an ostium, the array of radio-opaque markers having an elliptical pattern when the catheter is fluoroscopically imaged at a first angle oblique to a longitudinal axis of the catheter, and a linear pattern when the catheter is fluoroscopically imaged at a second angle in alignment with the longitudinal axis of the catheter.

2. The balloon catheter of claim 1 further comprising a guide wire lumen.

3. The balloon catheter of claim 1 further comprising a stent configured to be deployed at the ostium.

4. The balloon catheter of claim 1 wherein the array of dissimilarly shaped radio-opaque markers is configured to facilitate longitudinal positioning of the stent relative to the ostium.

5. The balloon catheter of claim 3 further comprising an occlusion element disposed at the distal end of the catheter.

6. The balloon catheter of claim 5 wherein the occlusion element comprises a balloon, the balloon comprises a compliant material, and a proximal portion of the balloon is more rigid than a distal portion of the balloon.

7. The balloon catheter of claim 6 wherein the balloon has an asymmetric shape when deployed.

8. The balloon catheter of claim 5 further comprising an aperture in a lateral wall of the catheter that communicates with a guide wire lumen, the aperture disposed between the dilatation balloon and the occlusion element.

9. The balloon catheter of claim 6 further comprising a reinforcing matrix embedded within the proximal portion of the balloon.

10. The balloon catheter of claim 6 further comprising a protective structure disposed to overlie the proximal portion of the balloon when deployed.

11. The balloon catheter of claim 10 wherein the protective structure comprises an expandable mesh or plurality of longitudinally extending struts.

12. The balloon catheter of claim 1 wherein the balloon catheter is configured to be delivered through a guide catheter having an articulable distal region and a control knob for articulating the distal region.

13. Apparatus for treating a renal vessel in the vicinity of a renal ostium, the apparatus comprising:
    a catheter having proximal and distal ends, including a balloon disposed on the distal end and coupled to an inflation port at the proximal end by an inflation lumen,
    the catheter comprising an array of discrete dissimilarly shaped radio-opaque marker segments permanently affixed at the distal end, each of the marker segments in the array disposed equidistant from the distal end and aligned about a predetermined circumference of the catheter to facilitate determination of placement and angularity of the catheter relative to the renal ostium, the array of marker segments having an elliptical pattern when the catheter is fluoroscopically imaged at a first angle oblique to a longitudinal axis of the catheter, and a linear pattern when the catheter is fluoroscopically imaged at a second angle in alignment with the longitudinal axis of the catheter.

14. The apparatus of claim 13, further comprising a selectively inflatable occlusion element disposed at a distance of between 0.2 cm and 2.5 cm from the balloon such that the occlusion element and balloon may be deployed simultaneously in a renal artery without interfering with each other.

15. The apparatus of claim 14 wherein the catheter further comprises an aperture in a lateral wall that communicates with the guide wire lumen, the aperture disposed between the balloon and the occlusion element, and the occlusion element is configured to occlude a guide wire lumen when deployed.

16. The apparatus of claim 13 wherein the array of radio-opaque marker segments is configured to facilitate longitudinal positioning of the catheter relative to the renal ostium.

17. The apparatus of claim 14 wherein the occlusion element comprises a compliant material, and a proximal portion of the occlusion element is more rigid than a distal portion of the occlusion element.

18. The apparatus of claim 17 wherein the occlusion element has an asymmetric shape when deployed in a renal artery.

19. The apparatus of claim 17 further comprising a reinforcing matrix embedded within the proximal portion of the occlusion element.

20. The apparatus of claim 14 further comprising a protective structure disposed to overlie a proximal portion of the occlusion element when deployed.

21. The apparatus of claim 20 wherein the protective structure comprises an expandable mesh or plurality of longitudinally extending struts.

22. The apparatus of claim 13 further comprising a guide catheter having an articulable distal region and a control knob for articulating the distal region.

23. The balloon catheter of claim 1, wherein the array of dissimilarly shaped radio-opaque markers is configured to facilitate rotational positioning of the catheter relative to the ostium.

24. The balloon catheter of claim 1, wherein the array provides a narrower elliptical pattern when the catheter is fluoroscopically imaged at a third angle.

25. The apparatus of claim 13, wherein the array of radio-opaque marker segments is configured to facilitate rotational positioning of the catheter relative to the renal ostium.

26. The apparatus of claim 13, wherein the array of radio-opaque marker segments is configured to provide a narrower elliptical pattern when the catheter is fluoroscopically imaged at a third angle.

* * * * *